United States Patent
Duggal et al.

(10) Patent No.: US 9,034,304 B2
(45) Date of Patent: May 19, 2015

(54) SUNSCREEN COMPOSITION

(75) Inventors: Charu Duggal, Bangalore (IN); Kumar Gaurav, Bangalore (IN); Janhavi Sanjay Raut, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 6 days.

(21) Appl. No.: 13/877,924

(22) PCT Filed: Sep. 12, 2011

(86) PCT No.: PCT/EP2011/065756
§ 371 (c)(1),
(2), (4) Date: May 28, 2013

(87) PCT Pub. No.: WO2012/048972
PCT Pub. Date: Apr. 19, 2012

(65) Prior Publication Data
US 2013/0280191 A1    Oct. 24, 2013

(30) Foreign Application Priority Data

Oct. 12, 2010 (IN) .......................... 2830/MUM/2010
Nov. 25, 2010 (EP) ..................................... 10192532

(51) Int. Cl.
*A61Q 17/04* (2006.01)
*A61K 8/368* (2006.01)
*A61K 8/35* (2006.01)
*A61K 8/36* (2006.01)
*A61K 8/37* (2006.01)
*A61K 8/86* (2006.01)

(52) U.S. Cl.
CPC . *A61K 8/368* (2013.01); *A61K 8/35* (2013.01); *A61K 8/361* (2013.01); *A61K 8/37* (2013.01); *A61K 8/86* (2013.01); *A61Q 17/04* (2013.01)

(58) Field of Classification Search
CPC ........... A61K 8/831; A61K 8/35; A61K 8/37; A61K 8/86; A61Q 17/04
See application file for complete search history.

(56) References Cited

U.S. PATENT DOCUMENTS

| 4,847,069 A | 7/1989 | Bissett |
| 4,954,332 A | 9/1990 | Bissett |
| 5,989,536 A | 11/1999 | Deckner |
| 6,607,713 B1 | 8/2003 | Chodorowski |
| 2004/0057918 A1 | 3/2004 | Chodorowski-Kimmes |

FOREIGN PATENT DOCUMENTS

WO    WO2008022946    2/2008

OTHER PUBLICATIONS

Meiyue Cosmetic, "Multi-effect beauty lotion SPF 10", Global New Products Database, Jul. 2010, pp. 1-2.
PCT International Search Report in PCT application PCT/EP2011/065756 dated Mar. 26, 2012 with Written Opinion.
European Search Report in EP application EP 10 19 2532 dated Apr. 19, 2011.

*Primary Examiner* — Lezah Roberts
*Assistant Examiner* — Nannette Holloman
(74) *Attorney, Agent, or Firm* — Rimma Mitelman

(57) ABSTRACT

The invention relates to a high SPF sunscreen composition. There is a problem of achieving high SPF while keeping the total amount of sunscreens in the compositions relatively low. It is desirable, that the enhanced SPF benefit could be achieved through synergistic interaction of commonly used ingredients, thereby the present applicants have been working on solving this problem and have surprisingly found that cosmetic compositions comprising dibenzoylmethane or its derivative in combination with an oil soluble UV-B sunscreen when incorporated in a sunscreen composition along with a non-ionic surfactant of a select class meeting certain HLB requirements, provide the enhanced SPF benefits when applied on the substrate of interest.

9 Claims, No Drawings

SUNSCREEN COMPOSITION

FILED OF THE INVENTION

The invention relates to a high SPF sunscreen composition.

BACKGROUND OF THE INVENTION

Solar radiation includes about 5% ultraviolet (UV) radiation, wavelength of which is between 200 nm and 400 nm. It is further classified into three regions: from 320 to 400 nm (UV-A), 290 to 320 nm (UV-B) and from 200 to 290 nm (UV-C). A large part of UV-C radiation is absorbed by the ozone layer. Scientific studies have indicated that exposure to UV-A and UV-B radiation for short period causes reddening of the skin and localized irritation, whereas continued and prolonged exposure can lead to sunburn, melanoma and formation of wrinkles. It is also reported that UV radiation causes significant damage to hair. Therefore, it is desirable to protect the skin and other keratinous substrates of the human body from the harmful effects of both, UV-A and UV-B radiation.

Various cosmetic preparations have been reported for preventing and/or protecting the skin from harmful effects of ultraviolet radiation. Numerous organic sunscreen agents capable of absorbing UV-A rays are reported in the field of cosmetics amongst which a particularly useful sunscreen is of the dibenzoylmethane class. Many UV-B sunscreens are also known and approved for safe use in personal care compositions for protection from UV-B radiation. Many cosmetic manufacturers prefer to include both UV-A and UV-B sunscreens in photoprotective compositions so as to provide protection over the entire range of UV radiation. Sun Protection Factor (SPF) is a commonly measured attribute of photoprotective compositions which indicates the protection that the skin gets from exposure to both UV-B and UV-A radiation.

Thus cosmetic manufacturers try to provide consumers with products having higher and higher SPF. One of the ways of achieving this is to incorporate high levels of UV-A and UV-B sunscreens. One disadvantage of this approach is the high cost associated with incorporation of high levels of sunscreens which are expensive. Further, there are safety and regulatory limitations on the upper limit of incorporation of these sunscreens. Sensory properties are also reported to get affected on incorporation of high levels of sunscreens. Hence, there is a problem of achieving high SPF while keeping the total amount of sunscreens in the compositions relatively low.

Various publications on more effective sunscreen compositions have been reported. US 2004/057918 (L'Oreal) discloses a photostable UV photoprotecting amount of at least one dibenzoylmethane organic sunscreen immobilized within a matrix prepared via sol-gel process from at least one silicon oxide, with at least one non-ionic surfactant and water, but in absence of any organic solvent.

U.S. Pat. No. 4,847,069 (P&G, 1989) discloses a pharmaceutical composition comprising sorbohydroxamic acid, or pharmaceutically acceptable salts thereof, and an anti-inflammatory agent, which are useful for topical application to prevent damage to skin caused by acute or chronic UV exposure. Combinations of sorbohydroxamic acid and an anti-inflammatory agent together with tocopherol sorbate and/or sun-screens are also disclosed.

WO 2008/022946 (Unilever) discloses a cosmetic composition comprising dibenzoylmethane or its derivative and p-methoxycinnamic acid or its derivative that minimizes degradation of the dibenzoylmethane when exposed to UV radiation by incorporating a combination of fatty alcohol ethoxylates and polyalkyleneglycol. The object of WO2008/022946 is to develop a composition that minimizes degradation of dibenzoylmethane UVA sunscreen when in use and exposed to sunlight (say for 30 or 60 minutes). The object of the present invention is to develop high SPF compositions i.e ones which provide high sun protection as measured at zero point in time with respect to exposure to sunlight. Thus knowledge of a composition that minimizes degradation of a UVA sunscreen when in use by exposure to UV radiation does not automatically lead one to the conclusion that this composition will exhibit high Sun Protection Factor at the initial point of exposure to the sun's rays.

Thus, while the above publications disclose certain sunscreen compositions with a few non-ionic surfactants, none of them disclose that a class of non-ionic surfactants, identified by the present inventors, when included in sunscreen compositions having low levels of organic sunscreens, provides for high SPF.

Therefore there exists a need for a personal care composition that is able to provide much higher SPF as compared to known sunscreen compositions but at low levels of sunscreen agents. It is desirable, that the enhanced SPF benefit could be achieved through synergistic interaction of commonly used ingredients, thereby giving the desired photoprotection benefits at substantially low costs.

The present applicants have been working on solving this problem and have surprisingly found that cosmetic compositions comprising dibenzoylmethane or its derivative in combination with an oil soluble UV-B sunscreen when incorporated in a sunscreen composition along with a non-ionic surfactant of a select class meeting certain HLB requirements, provide the enhanced SPF benefits when applied on the substrate of interest.

It is therefore an object of the present invention to obviate at least some drawbacks of the prior art and provide high SPF (equal to or higher than 20) photo-protective sunscreen composition.

Another object of the present invention is to achieve the above object using relatively low amounts of sunscreen agents thereby keeping costs low.

SUMMARY OF THE INVENTION

According to one aspect of the present invention there is provided a high SPF sunscreen composition comprising less than 8% by weight total organic sunscreens comprising,
a) 0.1 to 5% by weight dibenzoylmethane or its derivative;
b) 0.1 to 7% by weight an oil soluble UV-B organic sunscreen;
c) 0.1 to 5% by weight non-ionic surfactant selected from the class of alkyl phenol ethoxylates having HLB greater than 15
d) a cosmetically acceptable base.

According to another aspect of the present invention there is provided a use of a composition of the first aspect of the invention for obtaining a SPF higher than 20.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

By "A Sunscreen Composition" as used herein, is meant to include a composition for topical application to sun-exposed areas of the skin and/or hair of mammals, especially humans. Such a composition may be generally classified as leave-on or rinse off, and includes any product applied to a human body for also improving appearance, cleansing, odor control or general aesthetics. The composition of the present invention can be in the form of a liquid, lotion, cream, foam, scrub, gel, soap bar or toner, or applied with an implement or via a face mask, pad or patch. Non-limiting examples of such sunscreen compositions include leave-on skin lotions, creams, antiperspirants, deodorants, lipsticks, foundations, mascara, sunless tanners and sunscreen lotions and wash-off shampoos, conditioners, shower gels, toilet bars. "Skin" as used herein is meant to include skin on the face and body (e.g. neck, chest, back, arms, underarms, hands, legs, buttocks and scalp) and especially to the sun exposed parts thereof. The composition of the invention is also of relevance to applications on any other keratinous substrates of the human body other than skin e.g. hair where products may be formulated with specific aim of providing photoprotection.

By 'A High SPF sunscreen composition' is meant a composition that has an SPF higher than 20, more preferably higher than 25. The high SPF is achieved using total UV-B sunscreens in the range of 0.1 to 7%, preferably from 0.5 to 6%, more preferably 1 to 5%, by weight of the composition. It is an advantage of the present invention that the high SPF values are achieved by using low amount of total organic sunscreens. By low amount of total organic sunscreens is meant that the total amount of organic sunscreens is less then 8%, preferably less than 7%, further more preferably less than 6% by weight of the composition.

The invention provides for a high SPF sunscreen composition comprising, a UV-A sunscreen which is a dibenzoylmethane or its derivative; an oil soluble UV-B organic sunscreen in low amount; selective amount of a selective non-ionic surfactant; and a cosmetically acceptable base.

The composition of the invention comprises 0.1 to 5% by weight dibenzoylmethane or its derivative. Preferred dibenzoylmethane derivative are selected from 4-tert-butyl-4'-methoxydibenzoylmethane, 2-methyldibenzoylmethane, 4-methyl-dibenzoyl-ethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 2-methyl-5-isopropyl-4'-methoxydibenzoylmethane, 2-methyl-5-tert-butyl-4'-methoxy-dibenzoyl methane, 2,4-dimethyl-4'- methoxy dibenzoylmethane or 2,6-dimethyl-4-tert-butyl-4'-methoxy-dibenzoylmethane. The most preferred dibenzoylmethane derivative is 4-tert.-butyl-4'-methoxydibenzoylmethane. Dibenzoylmethane or its derivative is preferably present in 0.2 to 5%, more preferably 0.4 to 3%, by weight of the composition.

The composition of the invention comprises 0.1 to 7%, preferably from 0.5 to 6%, more preferably 1 to 5%, an oil soluble UV-B organic sunscreen by weight of the composition. The oil soluble UV-B organic sunscreen is preferably selected from the class of cinnamic acid, salicylic acid, diphenyl acrylic acid or derivatives thereof. A few of the preferred oil soluble UV-B sunscreens which are commercially available and useful for inclusion in the composition of the invention are sold under the brandname of Octisalate™, Homosalate™, NeoHelipan™, Octocrylene™ or Parsol MCX™. It is interesting to note that only use of oil soluble UV-B sunscreens in the composition of the present invention provide the enhanced SPF benefits of the invention while water-soluble UV-B sunscreens do not provide the desired benefits. It is preferred that the composition of the invention is substantially free of water soluble organic sunscreens. Water soluble sunscreens may however be incorporated in small amounts preferably less than 1%, further more preferably less than 0.5%, even further more preferably less than 0.1% by weight of the composition and optimally absent from the composition of the invention.

An important ingredient that contributes to enhancement of SPF of the sunscreen composition of the invention is a selective class of non-ionic surfactant. The non-ionic surfactant is selected from the class of alkyl phenol ethoxylates with HLB higher than 15. It is observed that use of ionic surfactants or non-ionic surfactants of the alkyl phenol ethoxylates class not meeting the claimed criteria do not provide as high an SPF enhancement. Additionally, it has been observed that other common non-ionic surfactants of the fatty alcohol ethoxylate class while providing some enhancement in SPF have a distinct disadvantage in that merely including a fatty alcohol ethoxylate surfactant causes inordinately high reduction in the viscosity of the compostion e.g. in creams and also loss of stability on extended storage. The inclusion of alkyl phenol ethoxylate surfactant not only provides higher SPF but there is no reduction in viscosity of the composition and high formulation stability over extended period of storage. Suitable examples of commercially available non-ionic surfactants for use in the composition of the invention are sold under the brand names of Triton X 165, Triton X 305, Triton 405, or Triton X 705. The non-ionic surfactant is included in 0.1 to 5%, preferably 0.2 to 3%, by weight of the composition.

The composition of the invention comprises a cosmetically acceptable base. The cosmetically acceptable bases are such as to have a product in preferably a cream, lotion, gel or emulsion format. It is preferred that the cosmetically acceptable base comprises 1 to 25%, more preferably 3 to 20%, further more preferably 5 to 20% fatty acid by weight of the composition. The cosmetically acceptable base preferably also comprises 0.1 to 10% soap by weight of the composition. A more preferred format is a cream, further more preferably one which has a vanishing cream base. Vanishing cream base is one which comprises 5 to 25% by weight fatty acid and 0.1 to 10% by weight soap. In such creams the fatty acid is preferably stearic acid and the soap is preferably potassium stearate. It is particularly preferred that cream compositions comprise higher than 5%, more preferably higher than 6% fatty acid by weight of the composition. It is particularly preferred that lotion compositions comprise higher than 1%, more preferably higher than 3% fatty acid by weight of the composition.

It has been observed that use of high levels of fatty acid also contributes to the high SPF. The cosmetically acceptable base is usually from 10 to 99.9%, preferably from 50 to 99% by weight of the composition. The cosmetically acceptable base preferably includes water. Water is preferably included in 35 to 90%, more preferably 50 to 85%, further more preferably 50 to 80% by weight of the composition.

Other useful sun-protective agents e.g. inorganic sunblocks may be preferably used in the present invention. These include, for example, zinc oxide iron oxide, silica, such as fumed silica, or titanium dioxide. The total amount of sun block that is preferably incorporated in the composition according to the invention is from 0.1 to 5% by weight of the composition.

The composition of the invention may additionally comprise a skin lightening agent. The skin lightening agent is preferably chosen from a vitamin B3 compound or its derivative e.g. niacin, nicotinic acid, niacinamide or other well known skin lightening agents e.g. aloe extract, ammonium lactate, azelaic acid, kojic acid, citrate esters, ellagic acid, glycolic acid, green tea extract, hydroquinone, lemon extract, linoleic acid, magnesium ascorbyl phosphate, vitamins like vitamin B6, vitamin B12, vitamin C, vitamin A, a dicarboxylic acid, resorcinol derivatives, hydroxycarboxylic acid like lactic acid and their salts e.g. sodium lactate, and mixtures thereof. Vitamin B3 compound or its derivative e.g.

niacin, nicotinic acid, niacinamide are the more preferred skin lightening agent as per the invention, most preferred being niacinamide. Niacinamide, when used, is preferably present in an amount in the range of 0.1 to 10%, more preferably 0.2 to 5% by weight of the composition.

The composition according to the invention may also comprise other diluents. The diluents act as a dispersant or carrier for other materials present in the composition, so as to facilitate their distribution when the composition is applied to the skin. Diluents other than water can include liquid or solid emollients, solvents, humectants, thickeners and powders.

The composition of the invention may comprise a conventional deodourant base as the cosmetically acceptable carrier. By a deodourant is meant a product in the stick, roll-on, or propellant medium which is used for personal deodorant benefit e.g. application in the under-arm or any other area which may or may not contain anti-perspirant actives.

Deodorant compositions can generally be in the form of firm solids, soft solids, gels, creams, and liquids and are dispensed using applicators appropriate to the physical characteristics of the composition.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

According to another aspect of the present invention there is provided a method of protecting the skin against UV radiation comprising the step of applying a composition of the present invention to the desired surface of skin.

According to yet another aspect of the present invention there is provided use of a composition of the first aspect of the invention for obtaining SPF higher than 20. The SPF is preferably higher than 25. The use is preferably for non-therapeutic benefits.

The invention is now further described by way of the following non-limiting examples.

EXAMPLES

Examples 1 to 12

Effect of Various Non-ionic Surfactants

Various compositions as shown in table 1 were prepared using different non-ionic surfactants. The difference between the various compositions were in the type of non-ionic surfactant used which are detailed in table 2. The SPF of the various compositions (examples 1-9) were measured and the results are shown in table 2. In-vitro SPF was measured using the Optometrics 290S instrument model. The substrate used was a 10 cm Transpore™ tape procured from 3M Company. The sample was applied at 2 mg/cm$^2$.

TABLE 1

| Ingredients | wt % |
|---|---|
| Stearic Acid | 15 |
| Parsol MCX ™ | 3 |
| Parsol 1789 ™ | 1.5 |
| Non-ionic surfactant | 2 |
| Polymer, Carbomer 980 | 1 |
| Niacinamide | 1 |
| Glycerine | 1 |
| Isopropyl myristate | 1 |
| Titanium dioxide | 1 |
| Glyceryl stearate | 1 |
| Mineral oil | 1 |
| Triethanol Amine | 0.5 |
| Potassium hydroxide | 0.5 |
| Cetyl alcohol | 1 |
| Silicone oil | 1 |
| Perfume | 0.5 |
| Methyl paraben + propyl paraben | 0.5 |
| Water | To 100 |

TABLE 2

| Example # | Non-ionic surfactant | Structure | HLB | SPF |
|---|---|---|---|---|
| 1 | IGEPAL CA 210 Polyethylene(2) octyl phenyl ether | C8Ph EO1.5 | 4 | 10 |
| 2 | Triton X 45 | C8Ph EO4.5 | 9.8 | 14.9 |
| 3 | IGEPAL CA 520 Polyethylene(5) octyl pheny ether | C8Ph EO5 | 10 | 16.6 |
| 4 | Triton X 114 | C8Ph EO 7.8 | 12.4 | 17 |
| 5 | Triton X 100 | C8Ph EO9.5 | 13.4 | 19 |
| 6 | IGEPAL CA 720 Polyethylene(12) octyl pheny ether | C8Ph EO12.5 | 14 | 19 |
| 7 | Triton X 102 | C8PhEO12 | 14.4 | 19 |
| 8 | Triton X 165 | C8Ph EO16 | 15.5 | 23.3 |
| 9 | Triton X 305 | C8Ph EO30 | 17.3 | 25 |
| 10 | Triton X 405 | C8Ph EO35 | 17.6 | 28.1 |
| 11 | Triton X 705 | C8Ph EO55 | 18.4 | 24.8 |

In table 2, the structure of the surfactant is denoted as CnPhEOm where Cn refers to the alkyl chain having n carbon atoms, Ph refers to a phenol group. EOm refers to m number of ethoxylate groups. The SPF number indicated was an average of three replicates.

The data in table 2 indicates that inclusion of a non-ionic surfactant meeting the critieria as claimed in this invention (examples 8 to 11) provides for enhanced SPF, while those that do not meet the criteria (examples 1 to 7) do not.

Example 12 to 14

Effect of Amount of Stearic Acid

Various compositions were prepared similar to example 10 except that the amount of stearic acid was varied. They were then tested for SPF similar to the method used for measuring SPF of example 1. The data is summarized in table 3.

TABLE 3

| Examples | Stearic acid concentration, wt % | SPF |
|---|---|---|
| Example 12 | 6% | 22 |
| Example 13 | 10% | 23.3 |
| Example 14 | 20% | 28.1 |

The data in table 5 indicates that use of more amount of stearic acid higher than 6% provides for higher values of SPF.

Examples 15 and 16

Effect of Inclusion of a Fatty Alcohol Ethoxylate Non-ionic Surfactant in Comparison to a Composition of the Present Invention and a Conventional Cream Composition Example 15 is a cream composition as per example 1 prepared using a non-ionic surfactant Brij 35 of the fatty alcohol ethoxylate class as was used in WO2008/022946. Example 16 is a conventional cream composition as per example 1 where no non-ionic surfactant was used.

The SPF of the compositions were measured as per procedure used for the previous examples. The viscosity of the compositions was measured using an AR-1000 model stress controlled Rheometer having a cone and plate geometry (cone: 40 mm diameter, 2 degrees, truncation: 58 micron) over a shear rate ranging from 0.1 to 1000 s$^{-1}$ at a temperature of 25° C. Each measurement over the above shear rate range was made over a time period of five minutes. Data on the viscosity of the samples at a representative shear rate of 1 s$^{-1}$ is shown in table 4. Further, the samples were observed visually, one month after the preparation of the compositions and the visual observation is summarized in table 4. Table 4 also provides the data for example 10.

TABLE 4

| Example | Non-ionic surfactant | SPF | Viscosity (Pa · S) | Visual appearance after 1 month of storage |
|---|---|---|---|---|
| 15 | Brij 35 | 27.0 | 2 | Emulsion appears to have separated with grain like particles suspended |
| 16 | None used | 9.7 | 20 | Appears similar to the sample when prepared |
| 10 | Triton X 405 | 28.1 | 18 | Appears similar to the sample when prepared |

Data in table 4 indicates that sample as per the invention (example 10) provides for a stable, high SPF composition. However when a composition is prepared as disclosed in prior art (example 15), the SPF obtained is lower, and has a major disadvantage of vastly reduced viscosity and instability over extended period of storage. The invention thus provides for a high SPF sunscreen composition comprising relatively low amounts of sunscreen compounds.

The invention claimed is:

1. A high SPF sunscreen composition comprising less than 8% by weight total organic sunscreens comprising,
   a) 0.1% to 5% by weight dibenzoylmethane or its derivative;
   b) 0.1 to 7% by weight an oil soluble UV-B organic sunscreen;
   c) 0.1 to 5% by weight non-ionic surfactant selected from the class of alkyl phenol ethoxylates having HLB higher than 15; and
   d) a cosmetically acceptable base,
   wherein said oil soluble UV-B organic sunscreen is selected from the group consisting of cinnamic acid, salicylic acid, diphenyl acrylic acid and derivatives thereof and wherein the composition has an SPF higher than 20.

2. A composition as claimed in claim 1 wherein said dibenzoyl methane derivative is 4-tert-butyl-4'-methoxydibenzoylmethane.

3. A composition as claimed in claim 1 wherein the cosmetically acceptable base is a cream, lotion, gel or emulsion.

4. A composition as claimed in claim 1 wherein the cosmetically acceptable base comprises 1 to 25% by weight fatty acid by weight of the composition.

5. A composition as claimed in claim 1 wherein said cosmetically acceptable base comprises 0.1 to 10% soap by weight of the composition.

6. A method of protecting the skin against UV radiation comprising the step of applying a composition as claimed in claim 1, to the desired surface of skin.

7. A method of obtaining SPF higher than 20 comprising the step of applying a composition as claimed in claim 1 to the desired surface of skin.

8. A composition as claimed in claim 1 wherein the composition has an SPF higher than 25.

9. A composition as claimed in claim 1 wherein the composition remains stable after one month of storage.

* * * * *